(12) United States Patent
Nakagawa et al.

(10) Patent No.: US 7,504,415 B2
(45) Date of Patent: Mar. 17, 2009

(54) THERAPEUTIC AGENT FOR GLOMERULAR DISEASE

(75) Inventors: Takashi Nakagawa, Hachioji (JP); Makoto Suda, Higashimurayama (JP); Yoichi Yamauchi, Komae (JP)

(73) Assignees: Kowa Co., Ltd., Nagoya-shi (JP); Nissan Chemical Industries, Ltd., Tokyo (JP)

( * ) Notice: Subject to any disclaimer, the term of this patent is extended or adjusted under 35 U.S.C. 154(b) by 481 days.

(21) Appl. No.: 10/474,194

(22) PCT Filed: Apr. 18, 2002

(86) PCT No.: PCT/JP02/03870

§ 371 (c)(1),
(2), (4) Date: Oct. 16, 2003

(87) PCT Pub. No.: WO02/085363

PCT Pub. Date: Oct. 31, 2002

(65) Prior Publication Data

US 2004/0116468 A1  Jun. 17, 2004

(30) Foreign Application Priority Data

Apr. 19, 2001 (JP) ............................. 2001-121058
Nov. 27, 2001 (JP) ............................. 2001-361257

(51) Int. Cl.
*A61K 31/47* (2006.01)
(52) U.S. Cl. ..................................... 514/311
(58) Field of Classification Search ............... 514/311
See application file for complete search history.

(56) References Cited

U.S. PATENT DOCUMENTS

| 5,102,888 | A | | 4/1992 | Fujikawa et al. |
| 6,090,839 | A | * | 7/2000 | Adams et al. ............... 514/415 |
| 6,147,109 | A | | 11/2000 | Liao et al. |
| 6,620,821 | B2 | * | 9/2003 | Robl ............ 514/290 |
| 2004/0116468 | A1 | | 6/2004 | Nakagawa et al. |

FOREIGN PATENT DOCUMENTS

| EP | 304063 | 2/1989 |
| EP | 482498 | 4/1992 |
| JP | 1-279866 | 11/1989 |
| JP | 8-198898 | 8/1996 |
| WO | 01/76573 | 10/2001 |
| WO | WO 02/17913 A1 | 3/2002 |
| WO | 02/30425 | 4/2002 |

OTHER PUBLICATIONS

Yazquez-Perez et al. Atorvastatin prevents glomerulosclerosis and renal endothelial dysfunction in hypercholesterolaemic rabbits. Nephrol. Dial. Transplant, 2000, vol. 16, Suppl. 1, pp. 40-44.*
Yoshimura et al. Simvastatin suppresses glomerular cell proliferation and macrophage infiltration in rats with mesangial proliferative nephritis. J. Am. Soc. Nephrol., 1998, vol. 9, pp. 2027-2039.*
Kajinami et al. NK-104: a novel synthetic HMG-CoA reductase inhibitor. Exp. Opin. Invest. Drugs, 2000, vol. 9, No. 11, pp. 2653-2661.*
Olbricht et al. Simvastatin in nephrotic syndrome. Kidney International, 1999, vol. 56, suppl. 71, pp. S113-S116.*
Buemi et al. Effect of fluvastatin on proteinuria in patients with immunoglobulin A nephropathy. Clin. Pharmacol. Ther., 2000, vol. 67, pp. 427-431.*
Imai et al. The effect of pravastatin on renal function and lipid metabolism in patients with renal dysfunction with hypertension and hyperlipidemia. Clin. and Exper. Hypertension, 1999, vol. 21, No. 8, pp. 1345-1355.*
Kei Matsushita et al.: "Effect of Fluvastatin on the Renal Function in Five-Sixths-Nephrectomized Rats". Nephron, pp. 398-399 2000.
Y-S Park et al.: "Lovastatin Reduces Glomerular Macrophage Influx and Expression of Monocyte Chemoattractant Protein-1 mRNA in Nephrotic Rats", American Journal of Kidney Diseases. vol. 31, No. 1, pp. 190-194 1998.
Ashio Yoshimura et al.: "Effect of simvastatin on proliferative nephritis and cell-cycle protein expression", Kidney International, vol. 56(Suppl)71, pp. S-84-S-87 1999.
U.S. Appl. No. 11/574,678, filed Mar. 5, 2007, Nakagawa.
Mitarai T. "Animal Models of Kidney Diseases, kidney and dialysis" Tokyo Igakusha 31:1991, pp. 436-439.
Stahl R.A.K., et al. "A Rat Model of Progressive Chronic Glomerular Sclerosis: The Role of Thromboxane Inhibition", Journal of the American Society of Nephrology, vol. 2, No. 11, 1992 pp. 1568-1577.

(Continued)

*Primary Examiner*—Ardin Marschel
*Assistant Examiner*—James D Anderson
(74) *Attorney, Agent, or Firm*—Oblon, Spivak, McClelland, Maier & Neustadt, P.C.

(57) ABSTRACT

The present invention is directed to a preventive or therapeutic agent for a glomerular disease comprising as an active ingredient a compound represented by formula (1):

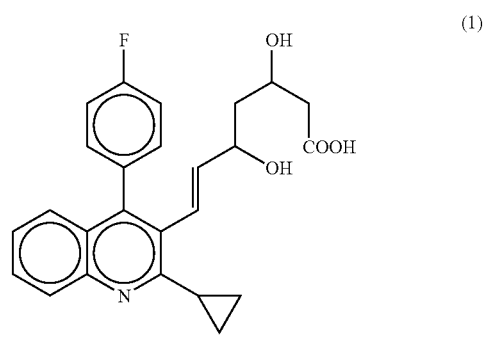

or a salt thereof. The preventive or therapeutic agent for glomerular diseases is useful for preventing or treating a variety of glomerular diseases including chronic glomerular nephritis.

14 Claims, 3 Drawing Sheets

OTHER PUBLICATIONS

Stahl R.A.K., et al., "Morphologic and Functional Consequences of immune-Mediated Mesangiolysis: Development of Chronic Glomerular Sclerosis", Journal of the American Society of Nephrology, vol. 2, Supplement 2, 1992, pp. S144-S148.

Floege J., et al., "Glomerular Cells, Extracellular Matrix Accumulation, and The Development of Glomerulosclerosis in the Remnant Kidney Model", Laboratory Investigation, vol. 66, No. 4, 1992, pp. 485-497.

Floege, J., et al., "Glomerular cell proliferation and PDGF expression precede glomerulosclerosis in the remnant kidney model", Kidney International, vol. 41 (1992), pp. 297-309.

* cited by examiner

Values represent mean value ± standard error
*: $p<0.05$ (vs. antibody-treated/solvent)

Values represent mean value ± standard error
**: $p<0.01$ (vs. antibody-treated/solvent)

THERAPEUTIC AGENT FOR GLOMERULAR DISEASE

TECHNICAL FIELD

The present invention relates to an agent useful for the prevention or therapy of glomerular diseases.

BACKGROUND ART

Glomerular diseases (primary glomerular nephritis), which develop in glomeruli of the kidneys, are clinically classified into seven types; i.e., acute nephritis after infection with hemolytic streptococcus, crescentic glomerulonephritis (rapidly progressive glomerulo nephritis), IgA nephropathy, membranous nephropathy, membranous proliferative nephropathy, focal glomerulonephritis, and minimal change nephrotic syndrome. Of these, the diseases other than acute nephritis after infection with hemolytic streptococcus, crescentic of glomerulonephritis, and minimal change nephrotic syndrome are generally called "chronic glomerular nephritis," but it remains to be elucidated about the cause and route of the onset of chronic glomerular nephritis. In the lesion processes chronic glomerular nephritis, most of them are generally progressive, and often result in renal failure.

In many cases, chronic glomerular nephritis is often recognized by a lesion occurring in glomeruli. The lesion is thought to largely associate with proliferation of mensagial cells (i.e., a type of constituent cells of a glomerulus) and an increase in the amount of the mensagial matrix (i.e., the extra-mensagial-cellular matrix). Recent studies have suggested that cytokines/growth factors, such as PDGF-BB and TGF-$\beta_1$, play an active role in causing a lesion in the mesangium (i.e., mesangial cells and the mesangial matrix). For example, PDGF-BB, which is produced from mesangial cells, is known to promote proliferation of the mesangial cells (Yoshimura A. et al, Kidney int., 40:470, 1991), and TGF-$\beta_1$ is known to promote synthesis and secretion of the mesangial matrix (Border W A. et al, Nature., 346:371, 1990).

Therefore, suppressing the response of mesangial cells to PDGF-BB or TGF-$\beta_1$ and inhibiting proliferation of mesangial cells and hyperplasia of the mensagial matrix are considered to be able to arrest the progress of a lesion occurring in the mensangium, and further to arrest the progress of a glomerular disease. Thus, a variety of such drugs (e.g., a mesangial cell proliferation inhibitor) have heretofore been investigated according to the pathological model (Fitner F. et al, Kidney int., 51(1)69, 1997).

However, an effective therapeutic agent for a glomerular disease has not been developed to date, and therefore, strong demand exists for the development of a novel drug exerting an excellent therapeutic effect on patients suffering from the aforementioned glomerular diseases.

Thus, an object of the present invention is to provide a preventive or therapeutic agent for a glomerular disease involving a lesion occurring in a glomerulus, particularly caused by a lesion in the mesangium.

DISCLOSURE OF THE INVENTION

In view of the foregoing, the present inventors have conducted intensive studies, and have found that a compound represented by formula (1) ((+)-(3R, 5S, 6E)-7-[2-cyclopropyl-4-(4-fluorophenyl)-3-quinolyl]-3,5-dihydroxy-6-heptenoic acid) inhibits a lesion occurring in the mesangium by inhibiting production of a mesangial matrix and therefore is useful as an effective preventive or therapeutic agent for a glomerular disease. The present invention has been accomplished on the basis of this finding.

Accordingly, the present invention provides a preventive or therapeutic agent for a glomerular disease comprising as an active ingredient a compound represented by formula (1):

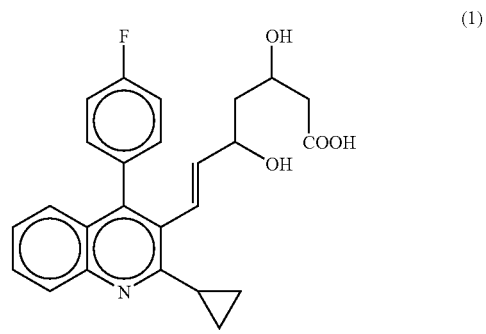

or a salt thereof.

The invention also provides use of the above compound or a salt thereof for producing a preventive or therapeutic agent for a glomerular disease.

Furthermore, the present invention provides a method for treating a glomerular disease characterized in that the method comprises administering the above compound or a salt thereof.

BEST MODE FOR CARRYING OUT THE INVENTION

Figure 1:
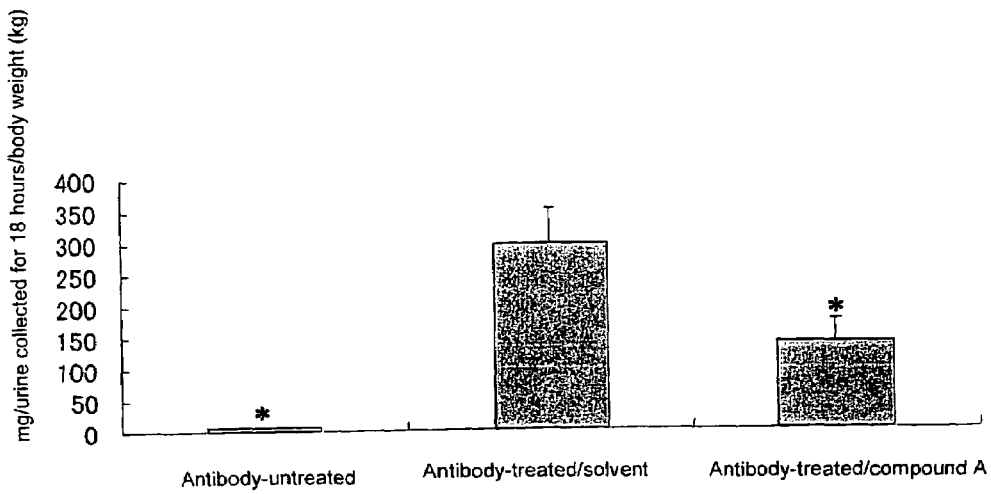
FIG. 1 is a graph showing the total amount of protein (18 hours) excreted in a urine sample collected from progressive anti-Thy-1 nephritic rats.

The compound of formula (1) or a salt thereof according to the present invention remarkably inhibits production of procollagen-type I.C peptide (PIP), which is an index for hyperplasia of the mesangial matrix, in a mesangial matrix production inhibition test (Example 1); remarkably inhibits, in a pharmacological test of progressive anti-Thy-1 nephritic rats, the amount of protein excreted in a urine sample and a lesion occurring in the malpighian tubes and the stroma (Example 2); inhibits a decrease in renal function of renal failure model rats (Example 3); and exhibits excellent safety (Example 4). Thus, administration of the compound prevents development of a lesion in the mesangium, leading to an arrest of the onset or progress of a glomerular disease. Therefore, the compound of formula (1) or a salt thereof is useful as a preventive or therapeutic agent for a variety of glomerular diseases including chronic glomerular nephritis (e.g., IgA nephropathy, focal glomerulonephritis, membranous nephropathy, and membranous proliferative nephropathy). In particularly, the compound or a salt thereof is useful as a preventive or therapeutic agent for a glomerular disease involving a lesion occurring in the mensagium.

The compound of formula (1) used in the present invention may be transformed into a pharmacologically acceptable salt thereof through a routine method. Examples of such a salt include alkali metal salts such as a sodium salt and a potassium salt; alkaline earth metal salts such as a calcium salt and a magnesium salt; and ammonium salts. Of these, a sodium salt and a calcium salt are preferred.

The compound of formula (1) or a salt thereof used in the present invention also encompasses a hydrate thereof and a solvate with a pharmaceutically acceptable solvent.

The compound of formula (1) includes stereoisomers with respect to its unsaturated bond and to an asymmetric carbon atom. The compound used in the present invention encompasses all such stereoisomers.

The compound of formula (1) or a salt thereof, which is a known compound exhibiting remarkably excellent HMG-CoA reductase inhibitory activity, can be produced through a method known per se or a similar method (see Japanese Patent No. 2,569,746, the specification of U.S. Pat. No. 5,856,336, and the specification of European Patent No. 0,304,063).

The compound of formula (1) or a salt thereof can be transformed, in accordance with directions for use, into a variety of pharmaceutical preparations. Examples of the dosage forms include powder, granules, fine granules, dry syrup, tablets, capsules, and injection.

These pharmaceutical preparations can be produced, in accordance with the dosage form, through a routine method by appropriately mixing with, diluting with, or dissolving in an medicinal additive such as an excipient, a disintegrant, a binder, a lubricant, a diluent, a buffer, a tonicity agent, a antiseptic agent, a wetting agent, an emulsifier, a dispersant, a stabilizer, or a solution adjuvant, and these additives can be used in pharmacy manufacturing.

Specifically, the powder formulation can be prepared by admixing the compound of formula (1) or a salt thereof with an appropriate optional additive such as an excipient or a lubricant. The tablet formulation can be prepared by admixing the compound or a salt thereof with an appropriate optional additive such as an excipient, a disintegrant, a binder, or a lubricant and pelletizing the formed mixture through a routine method. The thus-formed tablets may be coated in accordance with needs, thereby yielding film-coated tablets, sugar-coated tablets, etc.

The injection formulation may be in the form of a liquid formulation (aseptic solution or non-aqueous solution), an emulsion, or a suspension and is prepared in combination with a non-aqueous carrier, a diluent, a solvent, or a vehicle; for example, propylene glycol, polyethylene glycol, vegetable oil such as olive oil, and an injectable organic acid ester such as ethyl oleate. The above composition can be appropriately blended with adjuvants such as an antiseptic agent, a wetting agent, an emulsifier, or a dispersant.

The dose of the preventive or therapeutic agent of the present invention for a glomerular disease is appropriately determined according to the patient's body weight, age, sex, progress of the disease, or other factors in relation to the patient. In the case of peroral administration, the agent may be administered in a daily dose per adult of 0.01 to 100 mg as reduced to the compound of formula (1) or a salt thereof and may be administered singly or in a divided manner.

EXAMPLES

The present invention will next be described in more detail by way of examples.

Production Example

Production of monocalcium (+)-bis[(3R, 5S, 6E)-7-[2-cyclopropyl-4-(4-fluorophenyl)-3-quinolyl]-3,5-dihydroxy-6-heptenoate] (compound A)

Methyl [2-cyclopropyl-4-(4-fluorphenyl)-3-quinolyl]carboxylate was synthesized from 2-amino-4'-fluorobenzophenone according to a method described in J. Org. Chem., 2899 (1966). The above-mentioned compound A was synthesized from the methyl ester following the descriptions of Japanese Patent No. 2,569,746, U.S. Pat. No. 5,856,336, or Examples 1 to 3 disclosed in the specification of European Patent No. 0,304,063.

Example 1

Effect of Inhibiting Mensagial Matrix Production (1) Culture and Storage of Human Mensagial Cells Human mensagial cells (normal human mensagial cells, CryoNHMC, product of Sanko Junyaku Co., Ltd.) were cultured in MsGM medium (15 mL/flask) by use of two 75-cm$^2$ flasks (430720, CORNING). The medium was replaced with fresh medium every 2 to 3 days. Subsequently, the culture was scaled up to a 225-cm$^2$ flask (3000, COSTER) level, and three vials of passage 5 and 27 vials of passage 6 were prepared at a cell count of 5×10$^6$ cells/Cell Banker 1 mL/vial (430659, CORNING). The thus-cultured cell samples were stored in a container cooled by liquid nitrogen.

(2) Determination of Mansagial Matrix Production Inhibitory Activity

Cryopreserved human mensagial cells of passage 6 were revived and sown in a medium placed in a 75-cm$^2$ flask. The medium was replaced the next day, and incubation was continued for three more days. The thus-cultured cells were treated with 0.25% trypsin-0.02% EDTA. By use of a 96-well plate, solutions of compound A (1, 3, 10, 30 µmol/L) were added to the human mensagial cells (5760 cells/0.1 mL/well). Immediately after addition of compound A, TGF-$\beta_1$ (10 ng/mL) was further added, followed by culturing for 72 hours. Four wells were employed with respect to each compound A concentration. After completion of culturing, the PIP level of each culture liquid was determined through ELISA by use of a PIP determination kit (product of TAKARA). The percent inhibition (%) was calculated in accordance with the following equation, and the PIP production inhibitory activity (IC$_{50}$ value) was derived from the percent inhibition. The results are shown in Table 1.

Percent inhibition (%)=100×[(*PIP* amount with *TGF*-$\beta_1$ stimulation)−(*PIP* amount with *TGF*-$\beta_1$ stimulation after addition of compound *A*)]/[(*PIP* amount with *TGF*-$\beta_1$ stimulation)−(*PIP* amount without *TGF*-$\beta_1$ stimulation)]

TABLE 1

| | PIP production inhibitory activity (IC$_{50}$: µM) |
|---|---|
| compound A | 22.4 |

As is clear from Table 1, compound A inhibits, at a low concentration, PIP production which is caused by stimulation with TGF-$\beta_1$.

Example 2

Pharmacological Test Using a Progressive Anti-Thy-1 Nephritic Rat (1) Wistar female rats (5 weeks old, purchased from Japan SLC Co., Ltd.) were quarantined and acclimatized for four days, and used for the test. First, the right kidney of each rat was removed through flank incision under anesthesia with pentobarbital. Two weeks after removal of the right kidney, an anti-Thy-1 antibody (anti-mesangial-cell antibody/monoclonal antibody 1-22-3; purchased from Panafarm Laboratories Co., Ltd.) was intravenously administered (500 μg/rat) into the tail vein, whereby progressive anti-Thy-1 nephritis was induced. Immediately thereafter, compound A which had been suspended in an aqueous 0.5% sodium carboxymethyl cellulose solution was perorally administered via a peroral probe to each rat in a forced and continuous manner (20 mg/kg body weight, once/day, 10 weeks). After completion of 10 weeks' administration of compound A, urine was taken from each rat for 18 hours in a metabolic cage (Sugiyama Gen Co., Ltd.), and the total amount of protein excreted into the urine was determined.

As is clear from FIG. 1, the amount of protein excreted into urine is significantly lowered through administration of compound A.

(2) After completion of the urine analysis, the left kidney was extirpated from each rat, fixed in formalin, and embedded with paraffin. A thin slice obtained from the thus-treated kidney was stained with hematoxylin and eosin (HE), and observed under a stereoscopic microscope. Pathological-histological investigation of the thin slice was performed in accordance with a method described by Raij et al (Mesangial immune injury, hypertension, and progressive glomerular damage in Dahl rats, Kidney int. 26:137-143, 1984). Specifically, the entire area (coronary section) of the renal cortex was observed at a low magnification (objective, ×10), and the ratio of HE-stained lesion area to the total area was calculated. The ratio was evaluated on the basis of the following classification.

Figure 2:
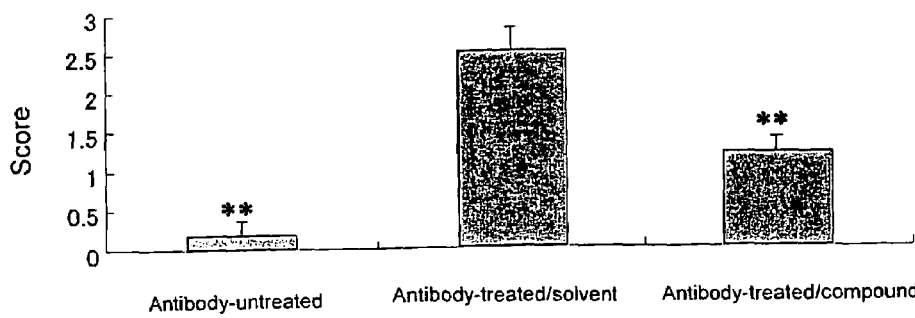
FIG. 2 is a graph showing the graded evaluation of a pathological finding tubulointerstital damage observed in progressive anti-Thy-1 nephritic rats.

Score 0: normal to almost normal
Score 1: lesion area of $\leq 10\%$
Score 2: lesion area of 10% to 30%
Score 3: lesion area of 30% to 50%
Score 4: lesion area of $\geq 50\%$ FIG. 2 shows the results. As is clear from FIG. 2., lesions occurring in the malpighian tubes and stroma (i.e., shrinkage or expansion of the malpighian tubes and fibrosis of the stroma around the malpighian tubes) are significantly inhibited through administration of compound A.

Example 3

Effect of the Present Invention on Renal Failure Model (5/6 Nephrectomized) Rats Male Wistar rats (10 weeks old, 300 to 350 g, purchased from Japan SLC Co., Ltd.) were anesthetized with pentobarbital, and the right kidney of each rat was extirpated. Subsequently, the left kidney was exposed. Under a stereoscopic microscope, two of the left renal artery branches (generally, one renal artery is separated into three branches) were ligated and one central branch was left intact, to thereby provide a 5/6 nephrectomized rat. When a renal artery branch is ligated, a portion controlled by the branch falls into ischemia, and such ischemic renal portion can be visually detected. The thus-produced renal failure models were evaluated in terms of increase in blood urea nitrogen level (BUN) one day after the ligation. Rats exhibiting a BUN (one day after the ligation) falling within a range of about 40 to 80 mg/dl were selected as the renal failure models.

The rats were divided into three groups such that the BUN level (one day after ligation) of the groups were equalized, and compound A was administered to each rat of the groups. The groups consisted of a normal rat group (N=5); a 5/6 nephphrectomized and drug-untreated group (control: N=8); and a 5/6 nephrectomized and compound-A-administered group (15 mg/kg: N=8). Compound A which had been suspended in an aqueous 0.5% sodium carboxymethyl cellulose solution was perorally administered once a day to each rat in a forced manner. The (total protein)/creatinine ratio (UP/Ucr) in a urine sample and the BUN level were determined on days 7, 14, 21, 28, and 35 after ligation. The results are shown in FIGS. 3 and 4.

Figure 3:
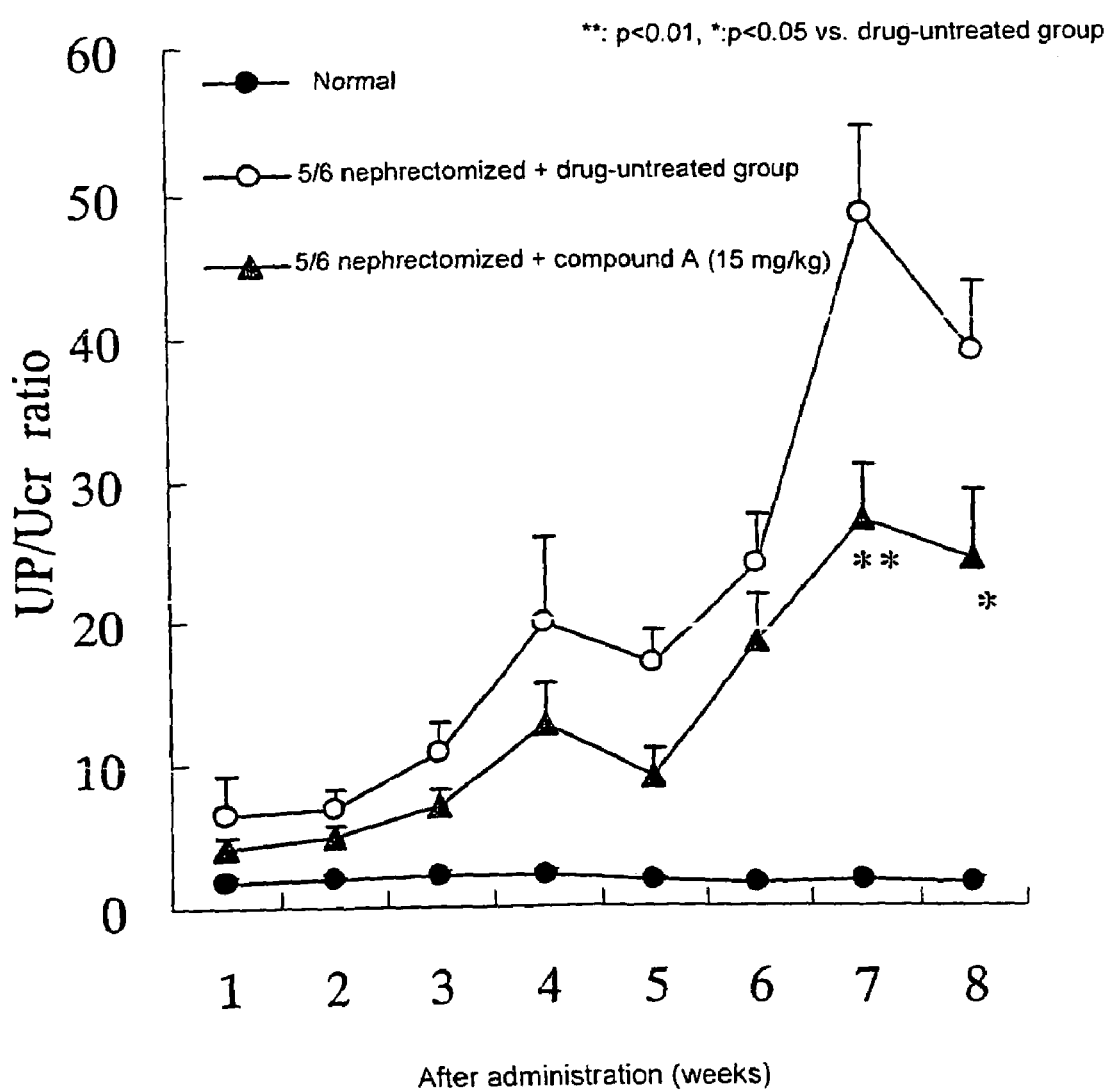
FIG. 3 is a graph showing time course in (total protein)/creatinine ratio of urine samples collected from renal failure model rats.

As is clear from FIG. 3, decrease in UP/Ucr has been confirmed in the compound-A-administered group at a comparatively early stage after administration. The UP/Ucr significantly decreases at weeks 7 and 8 after administration as compared with the drug-untreated group.

Figure 4:
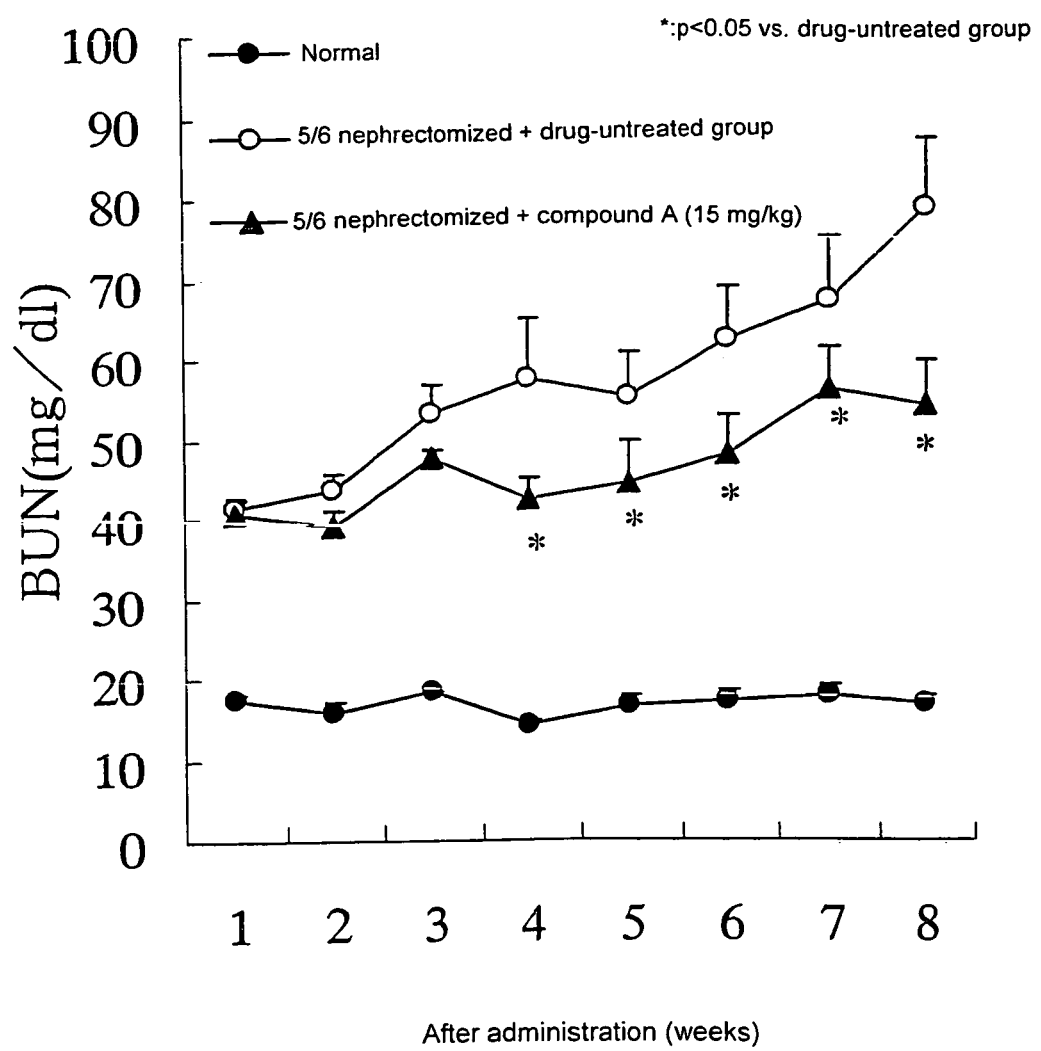
FIG. 4 is a graph showing time course in blood urea nitrogen level of blood samples collected from renal failure model rats.

As is clear from FIG. 4, in the compound-A-administered group, BUN level decreases from week 3 after administration, and significant decrease has been confirmed after week 4.

In this model, irreversible lesions such as glomerular sclerosis emerge after week 4. However, as described above, compound A inhibits an increase in BUN level (an index of decrease in renal function, i.e., a mediator for the irreversible lesions). This finding indicates that compound A would provide beneficial effects to patients suffering from renal disease. Thus, compound A is useful as a drug for arresting the progress of a glomerular disease.

Example 4

Acute Toxicity Test

Slc: Wistar rats (5 male rats and 5 female rats, 6 weeks old, purchased from Japan SLC Co., Ltd.) were subjected to fasting overnight. After fasting, compound A which had been suspended in an aqueous 0.5% sodium carboxymethyl cellulose solution was perorally administered in a forced manner to each male rat (500 mg/kg) and each female rat (250 mg/kg). During the observation period of 14 days, there occurred no case of death.

Example 5

Formulation of Drug Preparation

Tablets having the following composition per tablet were produced through the below-described procedure.

TABLE 2

| | |
|---|---|
| Compound A | 1.0 mg |
| Lactose | 101.4 mg |
| Low-substituted hydroxypropyl cellulose | 12.0 mg |
| Hydroxypropyl methyl cellulose 2910 | 2.0 mg |
| Magnesium metasilicate aluminate | 2.4 mg |
| Magnesium stearate | 1.2 mg |
| Total | 120.0 mg |

The ingredients from compound A through magnesium metasilicate aluminate were mixed, to thereby prepare a uniform powder mixture, and an appropriate amount of purified water was added to the mixture. The formed mixture was granulated through stirring granulation and pelletized. Magnesium stearate was added to the pelletized granules, and the mixture was pelletized again, to thereby produce tablets containing compound A.

INDUSTRIAL APPLICABILITY

The preventive or therapeutic agent of the present invention for glomerular diseases is useful for preventing or treating a variety of glomerular diseases including chronic glomerular nephritis (e.g., IgA nephropathy, focal glomerulonephritis, membranous nephropathy, and membranous proliferative nephropathy).

The invention claimed is:

1. A method for treating primary glomerular nephritis comprising:
   administering to a subject in need thereof a therapeutically effective amount of a compound represented by formula (1):

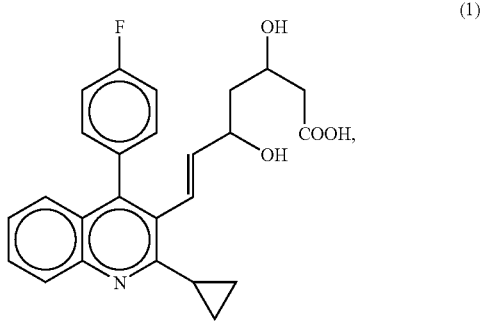

or a salt thereof.

2. The method of claim 1, comprising administering the compound of formula (1).

3. The method of claim 1, comprising administering a salt of the compound of formula (1).

4. The method of claim 1, comprising administering a mono-calcium salt of the compound of formula (1).

5. The method of claim 1, comprising administering an amount of said compound or salt of said compound that reduces the BUN (blood urea nitrogen) of said subject compared to a subject not receiving said compound or salt.

6. The method of claim 1, comprising administering an amount of said compound or salt of said compound that reduces the total protein/creatinine ratio (Up/Ucr) in said subject compared to a subject not receiving said compound or salt.

7. The method of claim 1, wherein the primary glomerular nephritis IgA nephropathy.

8. The method of claim 1, wherein the primary glomerular nephritis is focal glomerulonephritis.

9. The method of claim 1, wherein the primary glomerular nephritis is membranous nephropathy.

10. The method of claim 1, wherein the primary glomerular nephritis is membranous proliferative nephropathy.

11. The method of claim 1, wherein the primary glomerular nephritis is chronic glomerular nephritis.

12. The method of claim 1, wherein said compound or salt is administered by injection.

13. The method of claim 1, wherein said compound or salt is administered orally.

14. A method for treating glomerular nephritis comprising:
    administering to a subject in need thereof a therapeutically effective amount of a compound represented by formula (1):

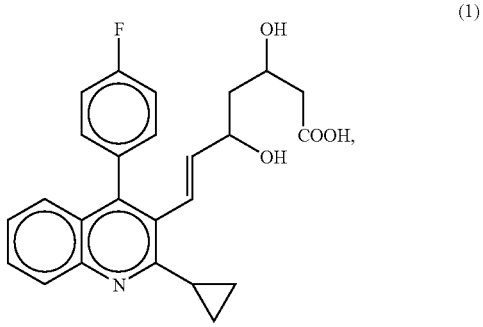

or a salt thereof.

* * * * *

UNITED STATES PATENT AND TRADEMARK OFFICE
CERTIFICATE OF CORRECTION

| | |
|---|---|
| PATENT NO. | : 7,504,415 B2 |
| APPLICATION NO. | : 10/474194 |
| DATED | : March 17, 2009 |
| INVENTOR(S) | : Nakagawa et al. |

It is certified that error appears in the above-identified patent and that said Letters Patent is hereby corrected as shown below:

On the cover page,

[*] Notice:  Subject to any disclaimer, the term of this patent is extended or adjusted under 35 USC 154(b) by 481 days.

Delete the phrase "by 481 days" and insert -- by 511 days --

Signed and Sealed this

Seventh Day of September, 2010

David J. Kappos
*Director of the United States Patent and Trademark Office*